(12) United States Patent
Kanzaki

(10) Patent No.: US 6,943,880 B2
(45) Date of Patent: Sep. 13, 2005

(54) SPECTROSCOPIC ELLIPSOMETER WITH ADJUSTABLE DETECTION AREA

(75) Inventor: Toyoki Kanzaki, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 512 days.

(21) Appl. No.: 10/128,379

(22) Filed: Apr. 23, 2002

(65) Prior Publication Data
US 2002/0159063 A1 Oct. 31, 2002

(30) Foreign Application Priority Data
Apr. 25, 2001 (JP) ........................................ 2001-127495

(51) Int. Cl.$^7$ .............................................. G01J 4/00
(52) U.S. Cl. ...................................................... 356/369
(58) Field of Search ................................. 356/364, 365, 356/366, 367, 368, 369

(56) References Cited

U.S. PATENT DOCUMENTS

| | | | |
|---|---|---|---|
| 5,166,752 A | * | 11/1992 | Spanier et al. ............... 356/369 |
| 5,517,312 A | | 5/1996 | Finarov |
| 5,608,526 A | | 3/1997 | Piwonka et al. |
| 5,764,365 A | | 6/1998 | Finarov |
| 5,798,837 A | | 8/1998 | Aspnes et al. |
| 5,963,327 A | | 10/1999 | He et al. |
| 5,969,818 A | | 10/1999 | Johs et al. |
| 6,128,085 A | | 10/2000 | Buermann et al. |
| 6,734,967 B1 | * | 5/2004 | Piwonka-Corle et al. ... 356/369 |

FOREIGN PATENT DOCUMENTS

| | | |
|---|---|---|
| WO | WO 92/12404 | 7/1992 |
| WO | WO02/079760 A3 | 10/2002 |

OTHER PUBLICATIONS

Estabil et al., "A Combined Spectroscopic Ellipsometer and Spectrophotometer", Solid State Technology, Washington, US, vol. 38, No. 4, Apr. 1995, pp. 71–72.

An Article Titled: Real–Time Spectroscopic Ellipsometry From 1.5 to 6.5 eV; By Zapien By, Collins & Messier, Thin Solid Films, 364 (2000), Mar. 27, 2000.

An Article Titled: "Dynamic Imaging Microellipsometry: Theory, System, Design, and Feasibility Demonstration", By Cohn, Wagener and Kruger, Appl. Opt. vol., 27(22), Nov. 15, 1988.

* cited by examiner

Primary Examiner—Gregory J. Toatley, Jr.
Assistant Examiner—Roy M. Punnoose

(57) ABSTRACT

A spectroscopic ellipsometer is provided for measuring a small target surface with a high degree of precision. An irradiating optical system provides a polarized light to the surface of the target, while a detecting optical system is provided with a higher F-number for collecting the reflected light from the target surface to introduce it into the spectrometer for measuring a thickness of a thin film on the surface of the sample in accordance with the polarization state of change of the detected light rays.

13 Claims, 3 Drawing Sheets

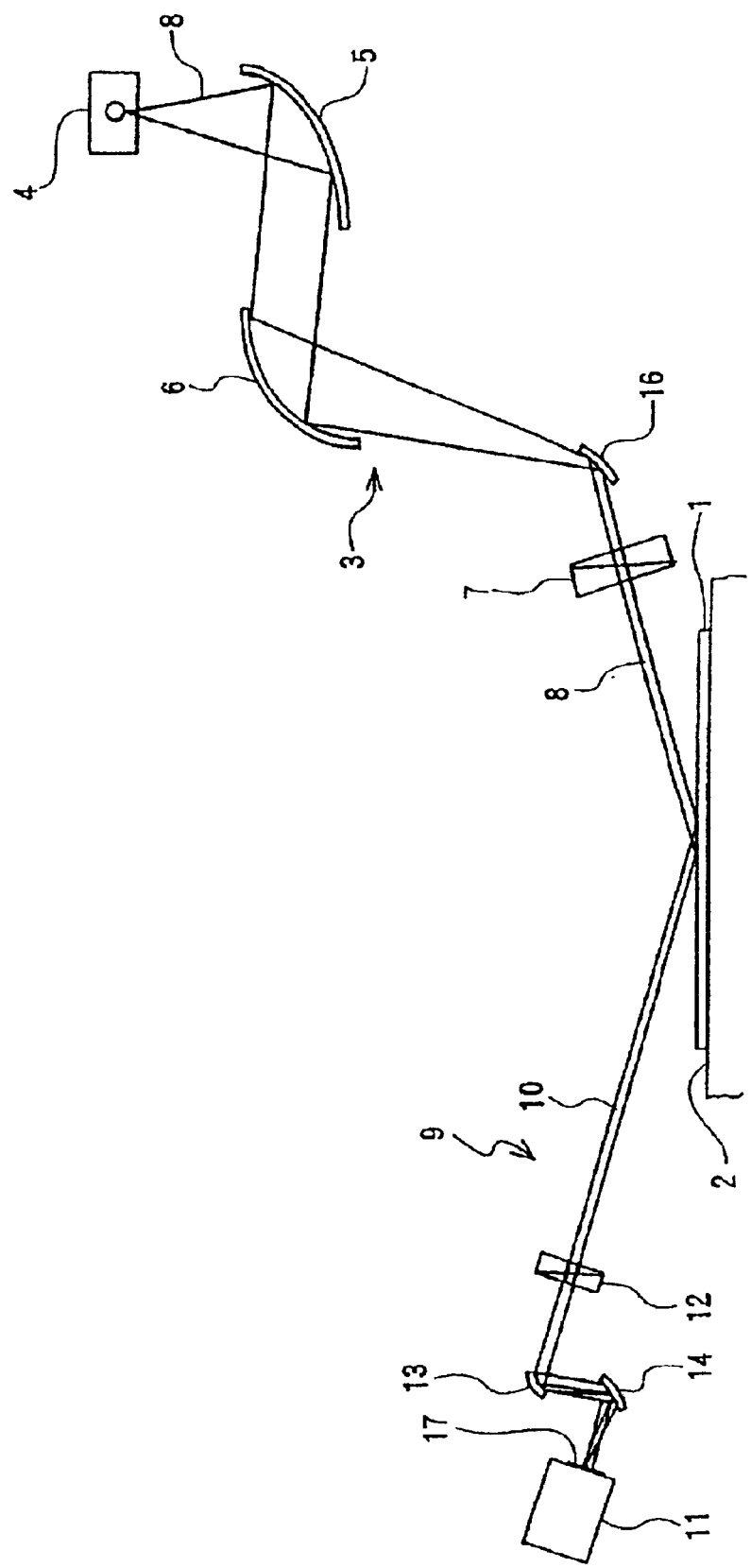

SPECTROSCOPIC ELLIPSOMETER WITH ADJUSTABLE DETECTION AREA

BACKGROUND OF THE INVENTION

1. Field of the Invention

The present invention relates to a spectroscopic ellipsometer for measuring the thickness of a thin film on surfaces of a target sample, such as a semiconductor wafer, a reticle/mask, a glass substrate of a liquid crystal display (LED) and the like, and more particularly for permitting a precise measurement of a selected area on a target surface.

2. Description of Related Art

A spectroscopic ellipsometer observes a change in the polarization state of light which reflects from the surface of a substance in order to measure optical constants (refractive index, extinction coefficient) of the surface, and if a thin film layer also exists on the surface of the substance, it can measure the film thickness and the optical constants of the thin film layer.

In a conventional spectroscopic ellipsometer, a F-number in an irradiating optical system has been equalized with a F-number in a detecting optical system, and the distribution range of the incidence angle of an irradiating light contacting the surface of the sample has been relatively wide. Since the spectroscopic ellipsometer determines objective values through an arithmetic processing based on the angle of incidence of the irradiating light, and a polarization characteristic of the irradiating light and a reflected light and the like, measurement to a high degree of precision becomes difficult if the distribution range of the incidence angle of the irradiating light is wide.

If, for this situation, the incidence angle of the irradiating light is intended to be kept constant, this can lead to the irradiation of a wide area of the surface of the sample, and therefore it is not possible to respond to a sample requirement of measuring only a relatively infinitesimal area.

In a spectroscopic ellipsometer, the angle of incidence of the irradiating light to the surface of the sample, a wavelength of the light and a polarization state are controlled, and the thickness, the refractive index (dielectric constant) and the like of the sample are estimated by arithmetic processing from the polarization characteristics of the reflected light and a reflection coefficient for each polarization component at the surface of the sample in each condition. Therefore, the angle of incidence of the irradiating light is an important controlling element from a measurement viewpoint and it is preferred that the irradiating light is a collimated light beam.

However, in actual fact, there are many situations that require measuring only a small area of the surface of the sample, and it is a general procedure to allow the irradiating light to have a certain magnitude of a solid angle to control a beam spot diameter of the irradiating light on the surface of the sample in such a case.

When light is condensed to a point using an optical system, a beam spot diameter d obtained is generally expressed by the following equation (1)

$$d = A \cdot \lambda \cdot Fno. \quad (1)$$

Wherein A is a constant, $\lambda$ is a wavelength, Fno. is a F-number and the F-number is a magnitude which is given by f/D where the diameter of an entrance pupil of the optical system is expressed by D and a focal length of the optical system is expressed by f.

As understood from equation (1) described above, it is necessary to reduce the F-number in order to reduce a beam spot diameter d. In this case, a gradient of the beam will come to have a gradient corresponding to the magnitude of the F-number. When the beam spot diameter d is reduced in this manner, the distribution of the gradient of the irradiating light becomes wide, but the case where the distribution of the gradient of the irradiating light is smaller will provide a higher measurement precision when the reflected light is introduced to a detector to detect signals.

The present invention has been made in consideration of the matters described above, and an object of the present invention is to provide a spectroscopic ellipsometer capable of measuring an extremely small area with a high degree of precision.

SUMMARY OF THE INVENTION

To achieve the above-mentioned object, a spectroscopic ellipsometer is provided with an irradiating optical system for irradiating a polarized light to the surface of a sample and a detecting optical system for outputting data with respect to the surface of the sample based on the amount of polarization state change of an elliptically polarized light reflected on the surface of the sample. A F-number in the above-mentioned irradiating optical system is set at a level to obtain the desired beam spot diameter at the surface of a sample, and an F-number of the above-mentioned detecting optical system is set to be higher than the F-number in the above-mentioned irradiating optical system.

BRIEF DESCRIPTION OF THE DRAWINGS

FIG. 3 is a view showing schematically the construction of a spectroscopic ellipsometer according to a third embodiment.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art of spectroscopic ellipsometers.

Figure 1:
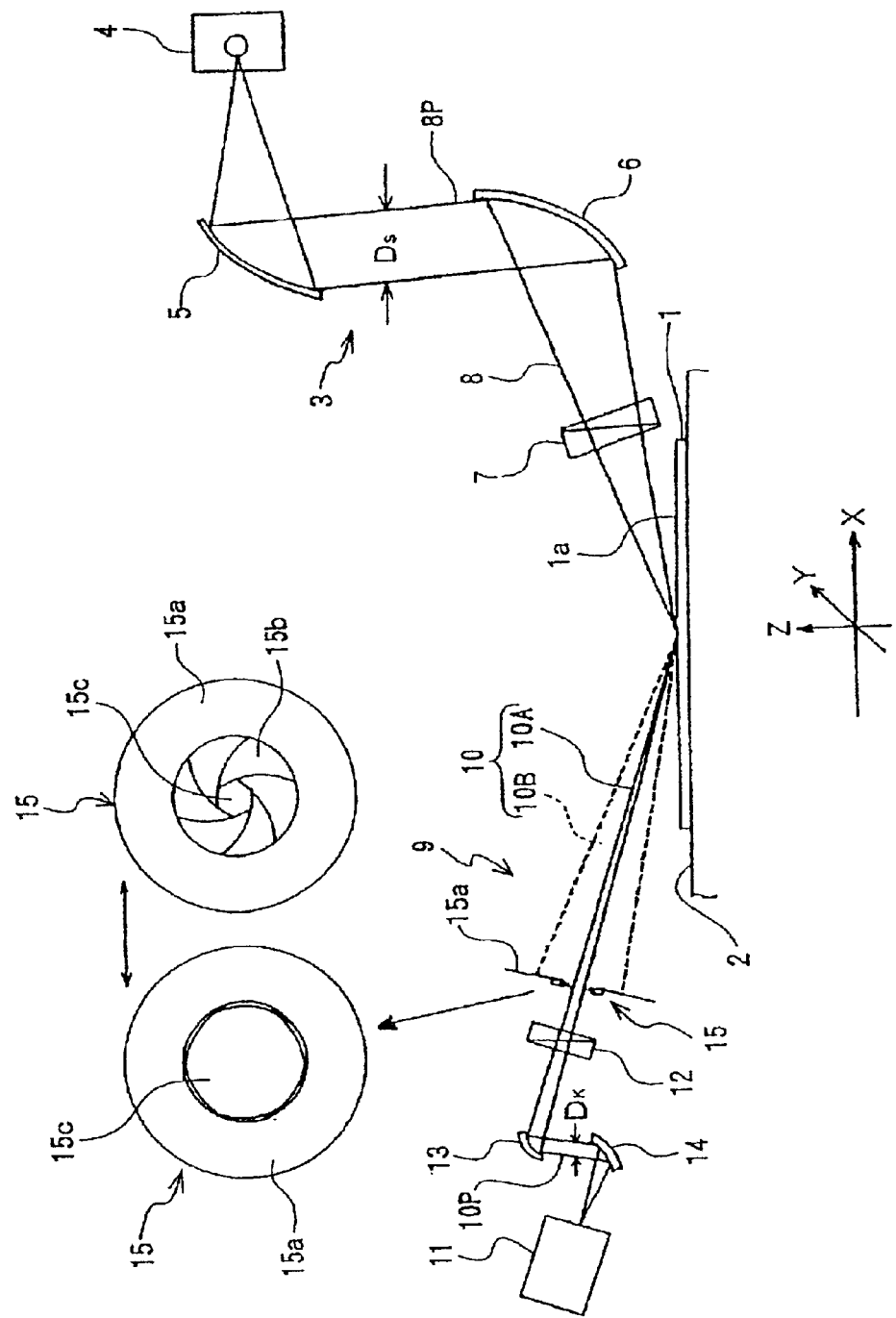
FIG. 1 is a view showing schematically the construction of a spectroscopic ellipsometer according to the first embodiment.

Hereinafter, the details of the present invention will be described in reference to the drawings. FIG. 1 shows schematically a construction of a spectroscopic ellipsometer according to a first embodiment of the present invention. In this drawing, a reference number 1 denotes a target sample (e.g., a semiconductor wafer) which is held horizontally on a sample stage 2. This sample stage 2 is constructed so as to hold the sample 1 on it with means such as a vacuum source and to move it linearly in three directions, e.g., X-direction (horizontal direction of the drawing), Y-direction (perpendicular direction to the drawing) and Z-direction (vertical direction parallel to the drawing), respectively, which are orthogonal to each other, with a stage-holding mechanism (not shown).

An irradiating optical system 3 is provided on one side above the sample stage 2, and includes a light source section 4, a pair of reflectors 5, 6, and a polarizer 7. The light source section 4 is provided with a white light source comprising, for example, a xenon lamp emitting light having a wide wavelength band of, for example, from 190 nm to 830 nm and a slit for reducing light (irradiating light) 8 emitted from the white light source to an appropriate diameter. The reflector 5, close to the light source section 4 comprises, for example, a concave mirror, and is installed so as to position the light source section 4 at the position of a focal point thereof, and therefore the irradiating light 8 directed from the reflector 5 to another reflector 6 is made to compose parallel rays of light having an appropriate diameter. The reflector 6 comprises, for example, a concave mirror, and receives the parallel rays of light 8P from the reflector 5 and condenses it through a polarizer unit 7 onto a specified target position of the surface 1a of the sample so as to form a specified beam spot diameter. The polarizer unit 7 linearly polarizes the irradiating light 8 from the reflector 6 in a specified direction. The reflectors 5 and 6 can include various types of mirrors to provide a focus point for imaging the light source such as spherical, parabolic, and elliptical mirrors.

When a diameter of the above-mentioned collimated light beam 8P from the light source section 4 is expressed by Ds and a focal length of the reflector 6 is expressed by fs, the F-number (hereinafter, referred to as Fno. s) of the above-mentioned irradiating optical system 3 is expressed by the following equation:

$$Fno.\ s = fs/Ds \qquad (2)$$

and the magnitude of the Fno. s is set at a sufficiently small value for attaining a beam spot diameter to be aimed at the surface 1a of the sample.

A reference number 9 denotes a detecting optical system provided on the other side of the sample above the sample stage 1, and when the linearly polarized light 8 is irradiated on the surface 1a of the sample, the detecting optical system 9 outputs the amount of polarization state change of an elliptically polarized light 10 reflected from the surface 1a of the sample, for example, to a spectrometer 11. The spectrometer 11 can comprise an analyzer 12, a pair of reflectors 13, 14, and a mask member 15. The reflector 13, closest to the analyzer 12, comprises, for example, a concave mirror, and is installed so as to position the surface 1a of the sample at the position of a focal point thereof, and makes the elliptically polarized light 10, passing through an aperture 15c (opening) of the mask member 15 parallel rays of light 10P to reflect it to another reflector 14. The reflector 14 comprises, for example, a concave mirror, and outputs the parallel rays of light 10P from the reflector 13 to the spectrometer 11. The mask member 15 has a function of an optical mask to pass only a light 10A at the center of the optical axis of the above-mentioned elliptically polarized light 10 and comprises, for example, a plate member 15a provided with a restricting member 15b being opening-adjustable freely, and is constructed in such a way that a degree of opening of the opening 15c has a shape such as a polygon in a plan view and is adjustable appropriately as shown in an enlarged view in the drawing. For example, a shutter mechanism can be utilized with an adjustable movement of the blades.

When a diameter of the above-mentioned parallel rays of light 10P is expressed by Dk and a focal length of the reflector 13 is expressed by fk, the F-number (hereinafter referred to as Fno. k) of the above-mentioned detecting optical system 9 is expressed by the following equation:

$$Fno.\ k = fk/Dk \qquad (3)$$

and the respective F-numbers are set in such a way that the following relationship holds between this Fno. k and the above mentioned Fno. s of the irradiating optical system 3.

$$Fno.\ s < Fno.\ k \qquad (4)$$

Furthermore, the above-mentioned detecting optical system 9 is formed so as to introduce only the light 10A having part of a solid angle about the objective angle of reflection to the spectrometer 11 by providing the above-mentioned mask member 15. When an extent of the opening 15c in the mask member 15 passes only light 10A representing a narrowing limit to the angle (solid angle), only the reflected light in the range of the narrow angle is obtained, and therefore, as apparent from the drawing, the light 10B in a portion designated by a reference character 10B, e.g., a space enclosed by a solid line while the space in a phantom line is significantly blocked. The solid angle of the reflected light 10 introduced to the detecting side of the spectrometer 11 is made to be an optimal value by adjusting the opening of the aperture 15c in the above-mentioned mask member 15 in consideration of the desired amount of light from the reflection and the distribution of the spectral sensitivity of the spectrometer 11.

In the spectroscopic ellipsometer constructed as described above, since the reflected light 10 from the surface 1a of the sample can be extracted with a small solid angle while a measurement area at the surface 1a of the sample is lessened by lessening the area irradiated by the irradiating optical system 3, it is possible to measure only a precise small area with a high degree of precision without lowering the quality of the measurement results.

In the above-mentioned first embodiment, the mask member 15 provided in the detecting optical system 9 is not limited to the position illustrated in the drawing, and it may be installed at any appropriate location in an optical path leading to the spectrometer.

When aberration (e.g., spherical aberration) which can affect the gradient of the light relating to a direction parallel to the drawing (X-direction) is sufficiently small, the aperture 15c in the mask member 15 formed in the form of a slit which extends linearly in the above-mentioned Y-direction may be provided in the irradiating optical system 3 depending on the position in the direction perpendicular to the drawing (Y-direction) in FIG. 1. Thus, the reflected light to be blocked is reduced, and the amount of light may be effectively limited.

Figure 2:
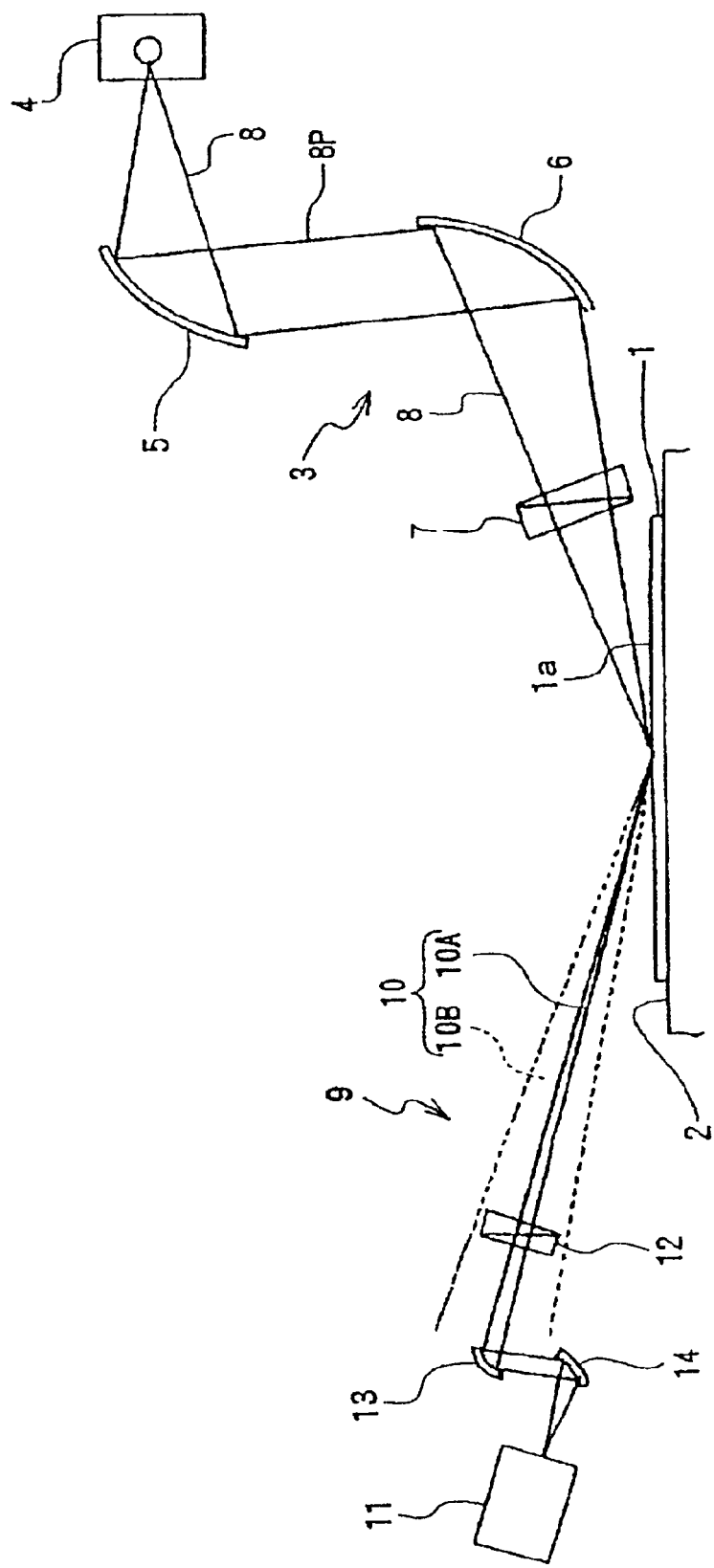
FIG. 2 is a view showing schematically the construction of a spectroscopic ellipsometer according to a second embodiment.

FIG. 2 shows a second embodiment of the present invention, and this embodiment omits the installation of the mask member 15 to the detecting optical system 9, and allows the optical elements such as reflector 13 to be orientated in such a manner to perform a similar function of the optical mask.

FIG. 3 shows a third embodiment of the present invention, and, in this embodiment, reflector 16 comprises, for example, a concave mirror 16 of a size and angular orientation between the reflector 6 and the polarizer 7, so that the irradiating light 8 to the surface 1a of the sample is made to be as close as possible to parallel rays of light. The F number of the irradiating optical system is set to be lower than the F number of the detecting optical system. A mask member 17 having a similar constitution to the above-mentioned mask member 15 is provided, for example, at the entrance of the spectrometer 11 of the detecting optical system 9.

The respective relationships of the F-numbers of the irradiating optical system 3 and the detecting optical system 9 in the second and the third embodiments described above are similar to that of the irradiating optical system 3 and the detecting optical system 9 in the first embodiment, and the actions and effects in these embodiments are also similar to that in the first embodiment.

As described above, in the present invention, it is possible to measure only an infinitesimal or very small area with a high degree of precision without lowering the precision of measurement. The spectroscopic ellipsometer is provided with an irradiating optical system for irradiating polarized light to the surface of the sample and a detecting optical system for outputting data with respect to the surface of the sample based on the amount of polarization state change of the elliptically polarized light reflected on the surface of the sample. The F-number in the above-mentioned irradiating optical system is set at a magnitude of level to be capable of obtaining a beam spot diameter at the surface of the sample, and the F-number of the above-mentioned detecting optical system is set to be higher than the F-number in the above-mentioned irradiating optical system. Therefore, it is possible to measure the infinitesimal area in various kinds of samples such as on a semiconductor wafer and a reticle/mask used in microelecronics technology and microminiaturization with a higher degree of precision.

What is claimed is:

1. In a spectroscopic ellipsometer having an irradiating optical system for irradiating a target and a detecting optical system for collecting the reflected light and providing the reflected light to a spectrometer, the improvement comprising:

a F-number for the irradiating optical system is lower than a F-number for the detecting optical system.

2. The spectroscopic ellipsometer of claim 1 wherein the detecting optical system includes a variable aperture masking member.

3. The spectroscopic ellipsometer of claim 1 wherein the irradiating optical system includes a pair of concave reflectors and a polarizer unit to provide a linear polarized light ray beam.

4. The spectroscopic ellipsometer of claim 3 wherein the detecting optical system includes from object to image side a variable aperture masking member, an analyzer, and a pair of concave reflectors.

5. The spectroscopic ellipsometer of claim 1 wherein the irradiating optical system includes a first pair of reflectors to focus light on a concave mirror which provides substantially parallel rays of light to a polarizer unit and subsequently to the target.

6. The spectroscopic ellipsometer of claim 5 wherein the detecting optical system includes an analyzer, a pair of concave reflectors and a masking member with a restricted aperture.

7. The spectroscopic ellipsometer of claim 1 wherein the detecting optical system includes a pair of concave reflectors relatively positioned and sized to provide the F-number larger than the F-number of the irradiating optical system.

8. The spectroscopic ellipsometer of claim 7 wherein the irradiating optical system includes a pair of concave reflectors and a polarizer unit.

9. A spectroscopic ellipsometer comprising:

an irradiating optical system for irradiating a target;

a detecting optical system for collecting the reflected light; and a spectrometer unit for analyzing the collected light, wherein a F-number for the irradiating optical system is lower than a F-number for the detecting optical system.

10. The spectroscopic ellipsometer of claim 9 wherein the irradiating optical system includes a first pair of reflectors to focus light on a concave mirror which provides substantially parallel rays of light to a polarizer unit and subsequently to the target.

11. The spectroscopic ellipsometer of claim 10 wherein the detecting optical system includes an analyzer, a pair of concave reflectors and a masking member with a restricted aperture.

12. A spectroscopic ellipsometer comprising:

an irradiating optical system includes a pair of concave reflectors and a polarizer unit to provide a linear polarized light ray beam to a target;

a detecting optical system includes a variable aperture masking member, an analyzer, and a pair of concave reflectors for collecting elliptically polarized collected light from the target; and a spectrometer unit for analyzing a polarization state change of elliptically polarized collected light;

wherein a F-number for the irradiating optical system is lower than a F-number of the detecting optical system.

13. The spectroscopic ellipsometer of claim 12 wherein the irradiating optical system further includes a third concave reflector of a size and orientation relative to the pair of concave reflectors to provide substantially parallel rays of light to the polarizer unit and subsequently to the target.

* * * * *